(12) United States Patent
Mangali et al.

(10) Patent No.: US 11,672,823 B2
(45) Date of Patent: Jun. 13, 2023

(54) CALCIUM GLUCONATE FORMULATION WITHOUT CALCIUM SACCHARATE

(71) Applicant: Nivagen Pharmaceuticals, Inc., Davis, CA (US)

(72) Inventors: Thirupathi Mangali, Davis, CA (US); Bala Tripura Sundari Chodavarapu, Davis, CA (US); Anand Shukla, Davis, CA (US); Jay Shukla, Davis, CA (US); Dasaradhi Lakkaraju, Davis, CA (US)

(73) Assignee: Nivagen Pharmaceuticals, Inc., Sacramento, CA (US)

( * ) Notice: Subject to any disclaimer, the term of this patent is extended or adjusted under 35 U.S.C. 154(b) by 0 days.

(21) Appl. No.: 17/871,058

(22) Filed: Jul. 22, 2022

(65) Prior Publication Data

US 2023/0043597 A1     Feb. 9, 2023

Related U.S. Application Data

(60) Provisional application No. 63/225,352, filed on Jul. 23, 2021.

(51) Int. Cl.
| | |
|---|---|
| *A61K 33/06* | (2006.01) |
| *A61K 47/02* | (2006.01) |
| *A61K 41/10* | (2020.01) |
| *A61K 9/08* | (2006.01) |

(52) U.S. Cl.
CPC .............. *A61K 33/06* (2013.01); *A61K 9/08* (2013.01); *A61K 41/10* (2020.01); *A61K 47/02* (2013.01)

(58) Field of Classification Search
None
See application file for complete search history.

(56) References Cited

U.S. PATENT DOCUMENTS

| | | |
|---|---|---|
| 1,965,535 A | 7/1934 | Pasternack et al. |
| 10,130,646 B1 | 11/2018 | Pizza |
| 10,342,813 B2 | 7/2019 | Pizza |
| 2015/0005380 A1 | 1/2015 | Boudy et al. |
| 2018/0110917 A1 | 4/2018 | Turzi |
| 2019/0076454 A1 | 3/2019 | Pizza |

FOREIGN PATENT DOCUMENTS

RU      2287988 C1    11/2006

OTHER PUBLICATIONS

Wang et al. (CN104490770A Machine English Translation) (Year: 2015).*

* cited by examiner

*Primary Examiner* — Robert A Wax
*Assistant Examiner* — Quanglong N Truong
(74) *Attorney, Agent, or Firm* — Ted Whitlock

(57) ABSTRACT

Described is an aqueous calcium gluconate solution formulated without calcium saccharate, which can be stored in a flexible plastic bag and can be terminally sterilized.

15 Claims, No Drawings

CALCIUM GLUCONATE FORMULATION WITHOUT CALCIUM SACCHARATE

FIELD OF THE INVENTION

The invention relates to an aqueous calcium gluconate solution formulated without calcium saccharate. The calcium gluconate solution can be stored in a flexible plastic bag and can be terminally sterilized.

BACKGROUND OF THE INVENTION

Calcium gluconate is used for treating individuals having low levels of calcium ions in their blood system. In serious calcium deficiency conditions, where life-threatening complications such as cardiac arrhythmia may result, intravenous (IV) administration of calcium may be necessary to rapidly increase the amount of calcium ions in the person's blood system. In most pediatric intensive care patients intravenously administered calcium gluconate is required.

Calcium gluconate is an old drug and has been commercially available as supersaturated aqueous solutions in 10 mL glass vials and 10 mL, 50 mL & 100 mL rigid plastic bottles. Mixtures of calcium gluconate with calcium saccharate are described in U.S. Pat. No. 1,965,535 ("the '535 patent"). The '535 patent teaches preparing calcium gluconate solutions containing calcium saccharate as a stabilizer which can be stored in glass containers after suitable sterilization or the use of a preservative agent. These supersaturated solutions require slow administration or dilution in a separate IV bag if administration at a faster rate is desired.

Glass vials can be disadvantageous due to the possibility of breakage. Glass vials and rigid plastic containers can also be disadvantageous because they take up more storage space than the flexible plastic bag products used for IV administration of drugs and other solutions.

Hospitals avoid the use of glass and rigid plastic vials and bottles in patient rooms and either will directly transfer the calcium gluconate from the container into plastic bags, which are then used for IV administration or have such bags prepared in advance at the hospital or by a compounder. However, these pre-prepared bags have a limited shelf life at room temperature, typically on the order of about 45 to 70 days. In contrast, the calcium gluconate solutions sold in glass and rigid plastic vials are reported to have shelf lives of about three years. As a result, hospitals cannot maintain a significant inventory of the calcium gluconate in the plastic IV bags.

More recently, WG Critical Care, LLC, (Paramus N.J., USA) has marketed terminally sterilized IV bags containing calcium gluconate in sodium chloride. These products are described and claimed in U.S. Pat. No. 10,130,646 ("the '646 patent") and U.S. Pat. No. 10,342,813 ("the '813 patent"). However, the products described in these patents issued to WG Critical Care, LLC, also contain calcium saccharate, which is a known preservative or stabilizer used in pharmaceutically acceptable formulations, and provides up to 4% of the calcium delivered to the patient.

Thus, there exists a need for a calcium gluconate aqueous solution product in plastic bags which has a long shelf-life, and which does not contain calcium saccharate, or which delivers 99-100% of the calcium from the calcium gluconate active ingredient.

SUMMARY OF THE INVENTION

The subject invention relates to an aqueous calcium gluconate solution without calcium saccharate. The calcium saccharate-free solution of calcium gluconate has a long-term storage stability when stored in a flexible plastic container.

The calcium gluconate solution in the flexible plastic container can be subjected to terminal sterilization via moist-heat autoclaving so that the product is in a sterile condition.

The calcium gluconate solution in the flexible plastic container, or "bag," can be administered to the patient using conventional IV technology.

The calcium gluconate solution of the invention can contain, in addition to the calcium gluconate, other non-calcium salts, such as sodium chloride or other electrolytes conventionally administered to patients in IV fluid therapy, but is free of additional calcium salts, including being free of calcium saccharate as a stabilizer.

The calcium gluconate solution of the subject invention provides at least 99% and up to 100% of the calcium ion to a patient in need thereof from the calcium gluconate ingredient contained within the solution. The calcium gluconate solution of the subject invention provides substantially no calcium to a patient from a calcium source other than calcium gluconate in the solution. Therefore, less than 1%, preferably less than 0.1%, and more preferably, 0% of the calcium delivered to the patient administered the claimed solution is derived from another ingredient in the solution of the invention, such as calcium saccharate.

DETAILED DESCRIPTION OF THE PREFERRED EMBODIMENTS

A preferred calcium gluconate aqueous solution of the invention is preferably a 1% or a 2% injectable solution of calcium gluconate. A 1% calcium gluconate aqueous solution can be prepared by adding about 10-11 mg/mL calcium gluconate, about 6-7 mg/mL of sodium chloride in water, at a pH between 6.0 and 8.2. A 2% calcium gluconate aqueous solution can be prepared by adding about 20-21 mg/mL calcium gluconate, about 6-7 mg/mL of sodium chloride in water, at a pH between 6.0 and 8.2. Sodium chloride is included in the formulations to provide an isotonic solution.

One preferred calcium gluconate aqueous solution of the invention comprises 20.90 mg/mL calcium gluconate, and 6.75 mg/mL sodium chloride, q.s. 1 mL of deionized water. For a 1000 mL batch, 20.90 g of calcium gluconate and 6.75 g of sodium chloride are mixed into 1000 mL deionized water (q.s. 1000 mL deionized water) and the pH can be adjusted as needed with 1N hydrochloric acid or 1N sodium hydroxide to between 6.0 and 8.2, more preferably adjusted to a pH 7.0±0.2.

The calcium gluconate aqueous solution of the invention is substantially free or free of calcium ion other than calcium ion provided by the calcium gluconate. For example, the calcium gluconate aqueous solution of the invention is free of calcium saccharate.

The calcium gluconate aqueous solution of the invention can be sterilized and more preferably can be terminally sterilized in the bag by heat sterilization.

The sodium chloride used in the formulation for isotonicity may be replaced in whole or in part by a sufficient quantity of potassium chloride or a different non-calcium salt, or a mixture of potassium chloride and a different non-calcium salt in an amount sufficient to provide an isotonic solution. A solution is considered to be isotonic if it has an osmolality of between about 260 and 320 mOsmol/kg.

The use of sugars such as dextrose should be avoided as they may negatively affect the stability of the solution when terminally sterilized and can adversely impact the storage life of the solution.

The calcium gluconate concentration in the formulation is limited only by its solubility in the aqueous medium. Concentrations ranging from about 0.5 wt. % to about 15 wt. % are preferred. More preferred are calcium gluconate concentrations of about 1 wt. % to 10 wt. %. A most preferred calcium gluconate concentration in the solution of the invention is about 1 wt. % or about 2 wt. %.

The amount of the tonicity adjusting agent added is usually an amount sufficient to make the solution isotonic. The tonicity adjusting agent may be omitted if an isotonic solution is not required or if the solution is sufficiently isotonic with an added tonicity adjusting agent. While sodium chloride is a common tonicity adjusting agent, any of the conventional tonicity adjusting agents may be used, provided the agent does not adversely impact the stability of the solution. In addition, because an advantage of the subject invention is the delivery of 99-100% of the calcium ion from the calcium gluconate, other or additional ingredients containing calcium ion are preferably avoided in the formulation of the subject invention.

One preferred composition comprises 20.90 mg/mL of calcium gluconate monohydrate, and about 6.75 mg/mL sodium chloride to adjust tonicity, and hydrochloric acid or sodium hydroxide to adjust the pH as needed. Other physiologically accepted acids and bases may be used to adjust the pH of the solution. Normally the pH is adjusted from about 5.5 to about 8.5, preferably from about 6 to about 8.2, and most preferably about 6.8 to about 7.2, wherein the target pH is 7.0.

Calcium gluconate solutions are known to be compatible with the following intravenous solutions and drugs: sodium chloride for injection 0.9%, lactated Ringer's injection, dextrose 5%-20%, dextrose-lactated Ringer's injection, dextrose-saline combinations, amikacin sulfate, aminophylline, ascorbic acid injection, bretylium tosylate, cephapirin sodium, chloramphenicol sodium succinate, corticotropin, dimenhydrinate, erythromycin gluceptate, heparin sodium, hydrocortisone sodium succinate, lidocaine HCl, methicillin sodium, norepinephrine bitartrate, penicillin G potassium/sodium, phenobarbital sodium, potassium chloride, tobramycin sulfate, vancomycin HCl, verapamil and vitamin B-complex with C.

The calcium gluconate solutions of the invention should be free of agents which will cause the calcium gluconate to precipitate from solution. Materials which may impact the calcium gluconate solutions include phosphate salts, oxytetracycline HCl, prochlorperazine edisylate, and tetracycline HCl. Compatibility is dependent upon factors such as pH, concentration, temperature, and diluents used. However, a preferred embodiment of the invention is free of an agent which can result in precipitation of the calcium gluconate, and is therefore preferably free of phosphate salts, oxytetracycline HCl, prochlorperazine edisylate, and tetracycline HCl.

Calcium gluconate is reportedly incompatible with the following solutions or drugs: intravenous fat emulsion, amphotericin B, cefamandole naftate, cephalothin sodium, dobutamine HCl, methylprednisolone sodium succinate, and metoclopramide HCl. A preferred embodiment of a solution according to the subject invention is free of intravenous fat emulsion, amphotericin B, cefamandole naftate, cephalothin sodium, dobutamine HCl, methylprednisolone sodium succinate, and metoclopramide HCl.

The flexible plastic container for containing a solution of the subject invention must be compatible with calcium gluconate. The flexible plastic container for containing a solution of the subject invention must also be able to undergo heat sterilization in moist steam without contaminating the calcium gluconate solution. Suitable flexible plastic containers are those made of copolymerized ethylene and vinyl acetate. Preferably the flexible plastic container, or "bag" used to contain a solution of the subject invention is laminated, having an inner-most layer comprising copolymerized ethylene and vinyl acetate. More preferably the bag comprises from 3 to 7 layers.

Materials used for a compatible flexible plastic container are commercially available under the tradename NEXCEL® by Sealed Air Corporation (Charlotte, N.C. USA.) The volume of the bag is dependent on the volume of premixed formula. The volume of premixed formula can be from 10 mL to 1000 mL, preferable 50 mL and 100 mL based on current calcium gluconate dosing. Larger or smaller volumes can be used depending on dosing requirements. CR3 elastomer copolyester ether bags may also be used for formulations to be sterilized in moist steam.

In an embodiment of the present invention, provided are a flexible plastic container with modified ports and closure system suitable for storing calcium gluconate formulations of the present invention which is subjected to sterilization by steam sterilization (e.g., autoclaving, 115° C.-121° C. for about 20 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g., PET, PEN, and the like), Teflon, Nylon, acetal (Delrin), polymethylpentene, PVDC, ethylvinylacetate, AN-copolymer, or the like. In addition to plastic bags, CZ resin containers, polypropylene and similar resins can be used as rigid containers and syringes.

The ports and the closure system preferably use commercially available polymers, elastomers, and the like. In an exemplary embodiment of the present invention, the administrative and additive ports can be made off external coextruded layer consists of synthetic thermoplastic rubber (Raumedic SRT320) ranging from about 20 to 30% based on an elastomer modified polypropylene. While the internal coextruded layer (PE770) of not more that 50% in composition consists of ethylene vinyl acetate without any further additives (EVA). The tubing ports can be made of two-layer materials, which can withstand both terminal sterilization and co-solvent matrix. Furthermore, the twist-off compositions can be made of polyproplene GRANUFLEX® 4489 between 70-80% and GRANUFLEX® 4371 15-20%. Alternatively, the port tube may be a bilayer tube comprising an outer layer of polypropylene and an inner layer of EVA and the twist off made of LDPE and PP. However, other polymers stable, low leachables, and without physical deformation during heat sterilization may also be used for the ports and closure assemblies.

Commercially available flexible plastic containers (bags) such as EXCEL® (Braun Company) comprising a three-layered ethylene-polypropylene bag having polyester elastomer outer layer, VISIV® (Hospira), NEXCEL® (Sealed Air), INTERVIA® (Baxter) preferably with a non-DEHP fluid path, Technoflex polyolefin bags, and the like, for pharmaceutical formulation or medical liquids are assembled of different plastic materials of different properties, thermal resistance, and functionalities. They are typically designed and tested for aqueous formulations admixtures, premixed, or ready-to-use pharmaceutical products.

The plastic container can be checked after sterilization for integrity before using it for the formulation. In addition, the formulation after sterilization can be analyzed for the presence of substances leached from the container as a result of the sterilization cycle.

In another alternative embodiment, provided are a flexible plastic container with modified ports and closure system suitable for storing calcium gluconate formulations of the present invention which is subjected to typically product sterilization by steam sterilization (e.g., autoclaving, 115° C.-121° C. for about 15 to 20 minutes) without altering the thermal properties of the film layers, ports and closure system as well as maintaining the integrity container.

Sterilization can preferably be accomplished by heat sterilization. Heat sterilization is normally performed using steam, preferably wet steam to allow for the use of pressure as a means of temperature control. The time period for the sterilization must be long enough to meet the sterility requirements required of an injectable product. When steam is used the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 20 minutes.

Having generally described this invention, a further understanding can be obtained by reference to certain specific examples, which are provided hereinbelow for purposes of illustration only, and are not intended to be limiting unless otherwise specified.

EXAMPLES

A. Batch Preparation Procedure
Batches were prepared in accordance with the following procedure steps:
Precautions:
 Nitrogen overlay/blanketing was used during all stages of compounding.
 Solution was not permitted to come in contact with any glass surface.
Steps:
i. Tare weigh the empty Stainless Steel compounding vessel with stirrer.
ii. Add >80% of required quantity of WFI in compounding vessel.
iii. Measure the pH of the WFI.
iv. Maintain the temperature of the WFI at 50 to 60° C. Measure the temperature of the WFI.
v. Weigh and add required quantity of Calcium Gluconate Monohydrate, USP to the compounding vessel and mix for not less than 60 min or until completely dissolved while maintaining the temperature at 50 to 60° C. Once dissolved measure the temperature of the solution.
vi. Weigh and add required quantity of Sodium Chloride to the compounding vessel and mix for 60 min or until completely dissolved while maintaining the temperature at 50 to 60° C. Once dissolved measure the temperature of the solution.
vii. Bring down the temperature of the solution to 20 to 25° C.
viii. Measure the pH of the solution.
ix. Optionally, adjust the pH to between 6-8.2, preferably 7.0±0.2 using 1N Sodium Hydroxide and/or 1N Hydrochloric Acid.
x. Measure the pH.
xi. Q.S. the batch with WFI to final target Volume. Mix thoroughly after QS for not less than 10 minutes.
xii. Measure the pH of the bulk solution.
xiii. Filter the bulk solution using 0.22-micron PVDF Filter.
xiv. Measure the Density of the bulk solution.

B. Batch #192053_92 formula was prepared in accordance with the Batch Preparation Procedure, above, and the formulation is summarized in Table 1, below:

BATCH FORMULA (Batch #192053_92)

TABLE 1

| Ingredient | CAS Number | Concentration | Batch Quantity |
|---|---|---|---|
| Calcium Gluconate Monohydrate USP | 71-27-2 | 20.90 mg/mL | 20.90 g |
| Sodium Chloride | 7647-14-5 | 6.75 mg/mL | 6.75 g |
| Hydrochloric Acid, NF, 1N | 7647-01-0 7732-18-5 | Adjust to pH 7.0 ± 0.2 | |
| Sodium Hydroxide, NF, 1N | 1310-73-2 7732-18-5 | Range 6.0 to 8.2 | |
| DI Water | N/A | Q.S. to 1 mL | Q.S. to 1000 mL |

C. Stability for Batch #192053_92
Solutions prepared in accordance with the procedure described above, and shown in Table 1, were placed on stability testing and the results are shown below in Table 2.

TABLE 2

| Product Name | Calcium Gluconate In Sodium Chloride Injection, 1000 mg per 50 mL (20 mL per mL) |
|---|---|
| Batch# | 192053_92 |
| API Mfg. & Lot # | Calcium Gluconate Monohydrate, USP: #CGN/1718004 |
| | Sodium Chloride: Avantor. #0000229148 |
| Stability | 25° C., 40% RH(LT), 40° C., 15% RH(ACC) |

| | pH | | | % Assay of Calcium | | | % Assay of Sodium Chloride | | | Osmolality (mOsmol/Kg) | | | Liquid particle count | | |
|---|---|---|---|---|---|---|---|---|---|---|---|---|---|---|---|
| Sample Name | 0 M | 3 M | 6 M | 0 M | 3 M | 6 M | 0 M | 3 M | 6 M | 0 M | 3 M | 6 M | 0 M | 3 M | 6 M |
| B#192053_92_LT | 6.5 | 6.5 | 6.6 | 101.2 | 101.3 | 103.4 | 101.2 | 101.2 | 103.1 | 296 | 309 | 306 | Pass | Pass | Pass |
| B#192053_92_ACC | 6.5 | 6.6 | 6.3 | 101.2 | 103.4 | 103.4 | 101.2 | 101.2 | 103.8 | | 307 | 306 | | Pass | Pass |
| RLD#90119_LT | 6.7 | NA | | 99.1 | NA | | 100.5 | NA | | 302 | NA | | Pass | NA | |

M: Month;
NA: Not Applicable

These results show that stability was maintained at three months and at six months, under room temperature and accelerated conditions, for all samples.

As can be seen from the results, the calcium gluconate solution was virtually unchanged after six months of accelerated stability testing. Accelerated conditions testing at six months is equivalent of 24 months at 25° C.±2° C. and 40%±5% relative humidity. These results are surprising in view of the prior art disclosures which teach that the presence of a stabilizer, such as calcium saccharide, is required in calcium gluconate bag formulations.

D. Batch #NCA22013 (10 mg/mL-50 mL fill volume) formula was prepared in accordance with the Batch Preparation Procedure, above, as summarized in Table 3, below

TABLE 3

| | |
|---|---|
| Product Name | Calcium Gluconate in Sodium Chloride Injection, 500 mg per 50 mL (10 mL per mL) |
| Batch Number | NCA22013 10 mg/mL-50 mL fill volume |
| API & Lot | Calcium Gluconate Monohydrate, USP # CGN/2021006 |
| Stability | 25° C., 40% RH (LT) and 40° C., 15% RH (ACC) |

E. Stability for Batch #NCA22013 (10 mg/mL-50 mL Fill Volume)

Solutions prepared in accordance with the procedure described above were placed on stability testing and the results are shown below in Table 4.

TABLE 4

| Tests | Specifications | Initial | 25° C., 40% RH (Long term) 3 Months | 40° C., 15% RH (Accelerated) 3 Months |
|---|---|---|---|---|
| Description | Clear colorless solution, free from visible particles | Complies | Complies | Complies |
| pH | Between 6.0 and 8.2 | 6.6 | 6.5 | 6.6 |
| Osmolality | 270 to 320 mOsmol/kg | 305 | 301 | 300 |
| Assay of Calcium | 95.0% to 105.0% | 101.3 | 100.6 | 99.1 |
| Assay of NaCl | 95.0% to 105.0% | 100.7 | 102.4 | 101.4 |
| Assay of Gluconate | 90.0% to 110.0% | 100.0 | 97.2 | 97.1 |
| Particulate Matters | 10 μm Particles: NMT 6000 25 μm Particles: NMT 600 | Complies | Complies | Complies |
| Aluminum | Not more than 25 ppb | Complies | Complies | Complies |

F. Batch #NCA22013 (10 mg/mL-100 mL fill volume) formula was prepared in accordance with the Batch Preparation Procedure, above, as summarized in Table 5, below:

TABLE 5

| | |
|---|---|
| Product Name | Calcium Gluconate in Sodium Chloride Injection, 1000 mg per 100 mL (10 mL per mL) |
| Batch Number | NCA22013 10 mg/mL-100 mL fill volume |
| API & Lot | Calcium Gluconate Monohydrate, USP # CGN/2021006 |
| Stability | 25° C., 40% RH (LT) and 40° C., 15% RH (ACC) |

G. Stability for Batch #NCA22013 (10 mg/mL-100 mL Fill Volume)

Solutions prepared in accordance with the procedure described above were placed on stability testing and the results are shown below in Table 6.

TABLE 6

| Tests | Specifications | Initial | 25° C., 40% RH (Long term) 3 Months | 40° C., 15% RH (Accelerated) 3 Months |
|---|---|---|---|---|
| Description | Clear colorless solution, free from visible particles | Complies | Complies | Complies |
| pH | Between 6.0 and 8.2 | 6.6 | 6.5 | 6.7 |
| Osmolality | 270 to 320 mOsmol/kg | 305 | 302 | 304 |
| Assay of Calcium | 95.0% to 105.0% | 101.3 | 99.1 | 99.1 |
| Assay of NaCl | 95.0% to 105.0% | 100.7 | 101.9 | 101.9 |
| Assay of Gluconate | 90.0% to 110.0% | 100.0 | 97.1 | 98.6 |
| Particulate Matters | 10 μm Particles: NMT 6000 25 μm Particles: NMT 600 | Complies | Complies | Complies |
| Aluminum Content | Not more than 25 ppb | Complies | Complies | Complies |

H. Batch #NCA21091 (20 mg/mL-50 mL fill volume) formula was prepared in accordance with the Batch Preparation Procedure, above, as summarized in Table 7, below.

TABLE 7

| | |
|---|---|
| Product Name | Calcium Gluconate in Sodium Chloride Injection, 1000 mg per 50 mL (20 mL per mL) |
| Batch Number | NCA21091 20 mg/mL-50 mL fill volume |
| API & Lot | Calcium Gluconate Monohydrate, USP # CGN/2021006 |
| Stability | 25° C., 40% RH (LT) and 40° C., 15% RH (ACC) |

I. Stability for Batch #NCA21091 (20 mg/mL-50 mL Fill Volume)

Solutions prepared in accordance with the procedure described above were placed on stability testing and the results are shown below in Table 8, below.

TABLE 8

| | | | 25° C., 40% RH (Long term) | | 40° C., 15% RH (Accelerated) | |
|---|---|---|---|---|---|---|
| Tests | Specifications | Initial | 3 Months | 6 Months | 3 Months | 6 Months |
| Description | Clear colorless solution, free from visible particles | Complies | Complies | Complies | Complies | Complies |
| pH | Between 6.0 and 8.2 | 6.8 | 6.6 | 6.6 | 6.6 | 6.5 |
| Osmolality | 270 to 320 mOsmol/kg | 299 | 298 | 297 | 298 | 299 |
| Assay of Calcium | 95.0% to 105.0% | 101.2 | 102.1 | 101.3 | 101.3 | 101.3 |
| Assay of NaCl | 95.0% to 105.0% | 100.3 | 99.9 | 99.5 | 99.9 | 100.1 |
| Assay of Gluconate | 90.0% to 110.0% | Not performed | 101.3 | 103.3 | 100.8 | 103.8 |
| Particulate Matters | 10 μm Particles: NMT 6000 25 μm Particles: NMT 600 | Complies | Complies | Complies | Complies | Complies |
| Aluminum Content | Not more than 25 ppb | Complies | Complies | Complies | Complies | Complies |

J. Batch #NCA21091 (20 mg/mL-100 mL fill volume) formula was prepared in accordance with the Batch Preparation Procedure, above, as summarized in Table 9, below.

TABLE 9

| | |
|---|---|
| Product Name | Calcium Gluconate in Sodium Chloride Injection, 2000 mg per 100 mL (20 mL per mL) |
| Batch Number | NCA21091 20 mg/mL-100 mL fill volume |
| API & Lot | Calcium Gluconate Monohydrate, USP # CGN/2021006 |
| Stability | 25° C., 40% RH (LT) and 40° C., 15% RH (ACC) |

K. Stability for Batch #NCA21091 (20 mg/mL-100 mL Fill Volume)

Solutions prepared in accordance with the procedure described above were placed on stability testing and the results are shown below in Table 10, below.

TABLE 10

| | | | 25° C., 40% RH (Long term) | | 40° C., 15% RH (Accelerated) | |
|---|---|---|---|---|---|---|
| Tests | Specifications | Initial | 3 Months | 6 Months | 3 Months | 6 Months |
| Description | Clear colorless solution, free from visible particles | Complies | Complies | Complies | Complies | Complies |
| pH | Between 6.0 and 8.2 | 6.8 | 6.7 | 6.8 | 6.6 | 6.6 |
| Osmolality | 270 to 320 mOsmol/kg | 299 | 299 | 297 | 298 | 299 |
| Assay of Calcium | 95.0% to 105.0% | 101.2 | 101.7 | 101.3 | 101.7 | 102.0 |
| Assay of NaCl | 95.0% to 105.0% | 100.3 | 100.5 | 99.5 | 99.9 | 100.1 |
| Assay of Gluconate | 90.0% to 110.0% | Not performed | 100.9 | 103.1 | 100.8 | 103.5 |
| Particulate Matters | 10 μm Particles: NMT 6000 25 μm Particles: NMT 600 | Complies | Complies | Complies | Complies | Complies |
| Aluminum Content | Not more than 25 ppb | Complies | Complies | Complies | Complies | Complies |

L. Batch #192053_92 (20 mg/mL-100 mL fill volume) formula was prepared in accordance with the Batch Preparation Procedure, above, without pH adjustment, as summarized in Table 11, below.

TABLE 11

| Product Name | Calcium Gluconate in Sodium Chloride Injection, 1000 mg per 50 mL (20 mL per mL) |
|---|---|
| Batch Number | 192053_92, 100 mL Fill volume |
| API & Lot | Calcium Gluconate Monohydrate, USP #CGN/1718004 |
| Stability | 25° C., 40% RH (LT) and 40° C., 15% RH (ACC) |

M. Stability for Batch #NCA21091 (20 mg/mL-100 mL Fill Volume)

Solutions prepared in accordance with the procedure described above (without pH adjustment) were placed on stability testing and the results are shown below in Table 12, below.

TABLE 12

| Tests | Specifications | Initial | 25° C., 40% RH (Long term) | | 40° C., 15% RH (Accelerated) | |
|---|---|---|---|---|---|---|
| | | | 3 Months | 6 Months | 3 Months | 6 Months |
| Description | Clear colorless solution, free from visible particles | Complies | Complies | Complies | Complies | Complies |
| pH | Between 6.0 and 8.2 | 6.5 | 6.5 | 6.6 | 6.6 | 6.3 |
| Osmolality | 270 to 320 mOsmol/kg | 296 | 309 | 306 | 307 | 306 |
| Assay of Calcium | 95.0% to 105.0% | 101.2 | 101.3 | 103.4 | 103.4 | 103.4 |
| Assay of NaCl | 95.0% to 105.0% | 101.2 | 101.2 | 103.1 | 101.2 | 103.8 |
| Particulate Matters | 10 μm Particles: NMT 6000 25 μm Particles: NMT 600 | Complies | Complies | Complies | Complies | Complies |

N. Batch #NCA21020 (20 mg/mL-100 mL fill volume) formula was prepared in accordance with the Batch Preparation Procedure, above, without pH adjustment, as summarized in Table 13, below.

TABLE 13

| Product Name | Calcium Gluconate in Sodium Chloride Injection, 2000 mg per 100 mL (20 mL per mL) |
|---|---|
| Batch Number | NCA21020-20 mg/mL 100 mL Fill volume |
| API & Lot | Calcium Gluconate Monohydrate, USP #CGN/1920001 |
| Stability | 25° C., 40% RH (LT) and 40° C., 15% RH (ACC) |

O. Stability for Batch #NCA21020 (20 mg/mL-100 mL Fill Volume)

Solutions prepared in accordance with the procedure described above (without pH adjustment) were placed on stability testing and the results are shown below in Table 14, below.

TABLE 14

| Tests | Specifications | Initial | 25° C., 40% RH (Long term) 12 Months | 40° C., 15% RH (Accelerated) 12 Months |
|---|---|---|---|---|
| Description | Clear colorless solution, free from visible particles | Complies | Complies | Complies |
| pH | Between 6.0 and 8.2 | 6.7 | 6.6 | 6.6 |
| Osmolality | 270 to 320 mOsmol/kg | 297 | 294 | 298 |
| Assay of Calcium | 95.0% to 105.0% | 99.1 | 98.4 | 98.4 |
| Assay of NaCl | 95.0% to 105.0% | 100.5 | 98.8 | 100.1 |
| Assay of Gluconate | 90.0% to 110.0% | Not performed | 100.1 | 100.2 |
| Particulate Matters | 10 μm Particles: NMT 6000 25 μm Particles: NMT 600 | Complies | Complies | Complies |

P. Batch #NCA21021 (20 mg/mL-100 mL fill volume) formula was prepared in accordance with the Batch Preparation Procedure, above, without pH adjustment, as summarized in Table 15, below.

TABLE 15

| Product Name | Calcium Gluconate in Sodium Chloride Injection, 2000 mg per 100 mL (20 mL per mL) |
|---|---|
| Batch Number | NCA21021-20 mg/mL 100 mL Fill volume |
| API & Lot | Calcium Gluconate Monohydrate, USP #CGN/1920001 |
| Stability | 25° C., 40% RH (LT) and 40° C., 15% RH (ACC) |

Q. Stability for Batch #NCA21021 (20 mg/mL-100 mL Fill Volume)

Solutions prepared in accordance with the procedure described above (without pH adjustment) were placed on stability testing and the results are shown below in Table 16, below.

TABLE 16

| Tests | Specifications | Initial | 25° C., 40% RH (Long term) 12 Months | 40° C., 15% RH (Accelerated) 12 Months |
|---|---|---|---|---|
| Description | Clear colorless solution, free from visible particles | Complies | Complies | Complies |
| pH | Between 6.0 and 8.2 | 6.7 | 6.5 | 6.5 |
| Osmolality | 270 to 320 mOsmol/kg | 297 | 297 | 296 |
| Assay of Calcium | 95.0% to 105.0% | 99.1 | 98.4 | 97.7 |
| Assay of NaCl | 95.0% to 105.0% | 101.2 | 98.8 | 99.5 |
| Assay of Gluconate | 90.0% to 110.0% | Not performed | 100.1 | 98.9 |
| Particulate Matters | 10 μm Particles: NMT 6000 25 μm Particles: NMT 600 | Complies | Complies | Complies |

Numerous modifications and variations of the present invention are possible in light of the above teachings. It is therefore to be understood that within the scope of the appended claims, the invention may be practiced otherwise than as specifically described herein. The invention described herein may be practiced in the absence of any element or elements, limitation or limitations which is not specifically disclosed herein. Thus, for example, in each instance herein, any of the terms "comprising," "consisting essentially of," and "consisting of" may be replaced with either of the other two terms. The terms and expressions are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:

1. A stable, aqueous calcium gluconate solution comprising:
about 1 to 15 wt. % calcium gluconates,
wherein said calcium gluconate solution is substantially free of calcium saccharate and is packaged in a flexible plastic container with water, the packaged calcium gluconate solution having a shelf-life greater than 12 months.

2. The solution of claim 1, wherein the calcium gluconate solution is isotonic.

3. The solution of claim 2, wherein the isotonic calcium gluconate solution comprises about 0.6 to 0.8 wt. % sodium chloride.

4. The solution of claim 1, wherein the flexible plastic container is a bag and the solution has a pH of from 6.0 to 8.2.

5. The solution of claim 1, wherein the water is deionized water or water for injection.

6. The solution of claim 1, wherein the calcium gluconate solution is free of a calcium ion-containing ingredient other than calcium gluconate.

7. The solution of claim 1, wherein the solution has a pH between about 6 and about 8.2.

8. The solution of claim 7, without pH-adjustment using an acid or base.

9. The solution of claim 7, wherein the pH is adjusted using 1N HCl or 1N NaOH.

10. The solution of claim 9, wherein the flexible plastic container is terminally sterilized by steam sterilization without altering the properties of the flexible plastic container.

11. The solution of claim 10, wherein the steam sterilization is autoclaving at 110° C.-130° C. for 10 to 30 minutes.

12. The solution of claim 1, wherein the water is water-for-injection.

13. The solution of claim 1, wherein the calcium gluconate solution comprises about 1 wt. % calcium gluconate.

14. The solution of claim 1, wherein the calcium gluconate solution comprises about 2 wt. % calcium gluconate.

15. The solution of claim 1, said solution having a shelf life between 12 months and 24 months.

\* \* \* \* \*